United States Patent [19]

Okuyama et al.

[11] Patent Number: 4,617,187

[45] Date of Patent: Oct. 14, 1986

[54] THERAPEUTIC METHOD FOR TREATING RADIATION ULCERS

[75] Inventors: Shinichi Okuyama; Hitoshi Mishina, both of Miyagi; Kazumaro Furuse, Tokyo; Isao Murotani, Kanagawa, all of Japan

[73] Assignee: Eisai Co., Ltd., Tokyo, Japan

[21] Appl. No.: 666,099

[22] Filed: Oct. 29, 1984

[30] Foreign Application Priority Data

Nov. 8, 1983 [JP] Japan ................................ 58-208395

[51] Int. Cl.$^4$ ...................... A61K 37/48; A61K 31/12
[52] U.S. Cl. ........................................ 424/94; 514/689
[58] Field of Search ........................... 424/94; 514/688

[56] References Cited

PUBLICATIONS

Okano et al–Chem. Abst., vol. 100, (1984), pp. 349d & 2203CS (subject index).

Seuref–Chem. Abst., vol. 99, (1983), p. 164,038p.

*Primary Examiner*—Sam Rosen
*Attorney, Agent, or Firm*—Wenderoth, Lind & Ponack

[57] ABSTRACT

Cutaneous administration of ubidecarenone, for example, application of ubidecarenone in the form of an ointment has been proven to be effective for treatment of various skin disorders caused by radiation, such as radiation ulcers and radiation dermatitis.

3 Claims, No Drawings

— 1 —

THERAPEUTIC METHOD FOR TREATING RADIATION ULCERS

BACKGROUND OF THE INVENTION (a) Field of the Invention

This invention relates to a therapeutic preparation for radiation ulcers which contains ubidecarenone as an effective component and also to a therapeutic method for radiation ulcers which features use of ubidecarenone.

(b) Description of the Prior Art

The radiotherapy for cancers has conventionally been prone to pay principal attention to the killing of cancer cells and to disregard the need for treatment of secondary problems or troubles developed on the skin by radiation, namely, radiation ulcers, radiation dermatitis or the like.

Generally speaking, skins which have been subjected to the radiotherapy are accompanied by intensive atrophy and their vascular walls have been rendered weak. These skins tend to undergo damages even by slightest extrinsic stimuli. The radiotherapy brings about such inherent side effects that it induces local obstructive aeterioloarteritis, destroys lymph vessels and the like and decreases SH-containing enzymes at certain local sites, thereby making the circulation of body fluid poor. On the other hand, strong tissues such as nervous tissues are able to survive the radiotherapy. Therefore, a metabolic disorder developed by poor circulation at a local site does not immediately stimulate nerves. If a disorder should be developed by an external cause such as extrinsic force on a skin which has been subjected to the radiotherapy, the disorder will be intractable and moreover, will spread to its surrounding skin. In addition, the patient will suffer from severer irritation and pains and the danger of mixed infection will increase as time goes on.

It is believed to be essential to achieve an immediate improvement to the circulation at such an infected site in order to treat the above-mentioned state of radiation ulcer or radiation dermatitis. Since such an infected site is clotted by inflammation products and the like, its treatment has hitherto been carried out by applying either singly or in combination the hyperbaric oxygen therapy, the glutathione injection therapy, the ascorbic acid and urokinase injection therapy, the oral cytochrome c administration therapy and so on. Furthermore, patients of this sort often develop some disorders at their hearts, livers, etc. Upon selection of drugs for radiation ulcers or radiation dermatitis, it is thus important to pay attention so that such additional disorders will also be cured without development of side effects. It is also recommended to prevent recurrence of such problems by using a tissue activator or the like even after the curing of radiation ulcers or radiation dermatitis, because the activity of the tissue of such an infected skin has been lowered.

The following publications (1)–(7), all in Japanese except for (5) and (7), will be listed by way of example for further-detailed explanation of the above prior art findings.

(1) Shiojima, S., Mishina H. and Ohuchi I.: Present Situation of Hyperbaric Oxygen Therapy in Tohoku Rosai Hospital. Nichiroshi, 21(8), 359–365, (1973);

(2) Mishina H., Haryu T., Shiojima S. and Imaizumi A.: Clinical Example of Radiation Ulcers. Shinryo to Shinyaku, 11(1), 105–110, (1974);

(3) Abe, Y., Shima T., Akiyama K. and Ohga H.: Treatment of Radiation Skin Disorders. Rinpo, 2(12): 19–25, (1967);

(4) Mishina H. and Haryu T.: Results of Application of Urokinase for Postoperative Breast Cancer after $^{60}Co$ Radiation. Medical View 7(1), 25–26, (1972);

(5) Guettier, Y. et al.: Cahiers D'O.R.L., 1, 77, (1966);

(6) Mishina H., Haryu T., Shiojima S., Imaizumi A. and Sato, T.: Hyperbaric Oxygen Therapy of Roentgen Ulcers. Basic Pharmacol Therapeut. 5, 1439, (1977); and (7) Sapiro, B.: Biochemical Mechanism in the Action of Radiation. In The Biological Basis of Radiation Therapy, E. E. Schwartz, ed., Lippincott, Philadelphia, 1966, pp. 31–59.

As mentioned above, radiation disorders are unavoidable for the carcinostatic radiation therapy. These disorders are intractable especially where they are accompanied by loss of tissue. Where scar tissue is spread over a wide area for example in a radiation ulcer, the epithelialization has proceeded to a considerable degree and the thus-infected skin has become weak against physical, chemical and biological influence. Therefore, its curing has become more difficult.

SUMMARY OF THE INVENTION

With the foregoing circumstances in view, the present inventors have studied various methods, which were led by the above-mentioned prior art methods, with a view toward achieving the treatment of radiation ulcers. As a result, it has been found that an administration of ubidecarenone to an ulcerated site leads to excellent curing results, leading to completion of this invention.

Accordingly, the overall object of this invention is to cure radiation ulcers. More specifically, an object of this invention is to provide therapeutic preparation and method effective for the curing of radiation ulcers.

In one aspect of this invention, there is thus provided a cutaneously-applicable therapeutic preparation for radiation ulcers which contains ubidecarenone as an effective component.

In another aspect of this invention, there is also provided a therapeutic method for radiation ulcers, which comprises cutaneously administering ubidecarenone.

The therapeutic preparation and method of this invention are effective for treating and curing radiation ulcers without development of noticeable side effects.

The above and other objects, features and advantages of the present invention will become apparent from the following description and the appended claims.

DETAILED DESCRIPTION OF THE INVENTION

The term "radiation ulcers" as used herein should be interpreted in broad sense. It means all disorders which skins have developed at radiated sites. Therefore, the above term embraces not only those proceeded to actual ulcers but also those including radiation dermatitis. In other words, the effectiveness of the present invention has been proven as a result of an observation on its effects which observation was carried out using as samples those already proceeded to ulcers. As readily envisaged from the above observation, the present invention is also effective for intermediary disorders in each of which the destruction of tissue has not proceeded to an ulcer.

Ubidecarenone is also called ubiquinontene or coenzyme $Q_{10}$ and has already been used as a therapeutic agent for congestive heart failure in the pharmaceutical field. The same ubidecarenone is also useful in the practice of this invention. Ubidecarenone is extracted from mitochondria of bovine cardiac muscle and is known to take part in the electron transport system. Corollary to this, ubidecarenone can improve the percentage oxygen utilization of cardiac muscle and maintain the ATP-yielding function at a high level even when the cardiac muscle is in an ischemic state. As a result, it has been known that ubidecarenone can reduce disorders, which the tissue of ischemic cardiac muscle would develop, and can hence improve the drop of heart contraction function.

There has however been absolutely unknown the fact that radiation ulcers can be successfully cured by cutaneously-administered ubidecarenone. This surprising effects of ubidecarenone have been uncovered for the first time by the present inventors.

Ubidecarenone is crystalline powder of a yellow to orange color with a melting point of 48°–52° C. It is oil-soluble but is hardly soluble in water or methanol. As mentioned above, it has hitherto been perorally administered for the improvement of various symptom of congestive heart failure. For the sake of reference, its subacute toxicity and chronic toxicity upon peroral administration are as follows:

Subacute toxicity

Ubidecarenone was perorally administered at 40, 200 and 1,000 mg/kg/day to male and female Wistar rats continuously over a period of 5 weeks and also at 60 and 600 mg/kg/day to male and female rabbits continuously over a period of 23 days. No differences were observed in general appearance, blood, urine test and morphological observation (both visual and histological) between the thus-treated rats and rabbits and those of a control.

Chronic toxicity

Ubidecarenone was forcedly and perorally administered at 6, 60 and 600 mg/kg/day to female and male Wistar rats continuously over a straight period of 26 weeks. As a result, no differences were observed in general appearance, blood, urine test and morphological observation (both visual and histological) between the thus-treated rats and those of a control.

The present invention features cutaneous administration of ubidecarenone to a site where such a radiation ulcer as defined above has developed.

For its cutaneous administration, ubidecarenone may be applied, as is, directly to such an infected site but it is desirable to apply it in the form of a preparation suitable for its coating onto the skin whenever possible. Furthermore, it is also feasible to administer ubidecarenone in combination with other drugs, for example, cytochrome c, urokinase and/or the like. It should however be borne in mind that the present invention is not necessarily limited to such a combined use of other drugs.

The content of ubidecarenone in the therapeutic preparation according to this invention may be recommended to be 0.05–5.0% or more preferably, 0.1–2.0%. The therapeutic preparation may be applied in a suitable amount, depending on the size and progress of each ulcer.

When applied to the skin, ubidecarenone exhibits good stability and little irritation to the skin. Table 1 shows by way of example results of various tests, i.e., the primary skin irritation, cumulative irritation, blepharoirritation, photo-toxicity, challenge, optical challenge and patch test.

| Test | Conc. | Solvent | | Results/Conclusion |
|---|---|---|---|---|
| Primary irritation | 1% | Squalane | 0.1 | Little skin irritation |
| | — | " | 0.1 | Little skin irritation |
| Cumulative skin irritation | 1% | " | 0.3 | Little skin irritation |
| | — | " | 0.3 | Little skin irritation |
| Blepharo-irritation | 1% | " | | Little blepharo-irritation |
| | — | " | | Little blepharo-irritation |
| Phototoxicity | 1% | " | (−) | Little phototoxicity |
| | 10% | " | (−) | Little phototoxicity |
| Challenge (Adjuvante & Patch Method) | Induction: 5% Acetone | | | |
| | 5% | Acetone | 0/10 | Little challenge |
| | 1% | " | 0/10 | Little challenge |
| Photo-challenge (Adjuvante Strip method) | Induction: 10% Acetone | | | |
| | 10% | Acetone | 0/5 | Little photo-challenge |
| | 5 | " | 0/5 | Little photo-challenge |
| | 2 | " | 0/5 | Little photo-challenge |
| | 1 | " | 0/5 | Little photo-challenge |
| | 0.5 | " | 0/5 | Little photo-challenge |
| Patch test | 1% | Squalane | 0/54 | Little skin irritation |
| | — | " | 0/54 | Little skin irritation |

In order to form ubidecarenone into a preparation suitable for cutaneous administration, one or more excipients or vehicles which causes little irritation may be suitably chosen. For example, glycerin, hohoba oil, cetyl alcohol, olive oil, a glyceryl fatty acid ester and/or the like may be selected to prepare a preparation for cutaneous administration in a manner known per se in the art.

Effects of the present invention will next be described in the following case reports:

Case 1

Female, 68 y.o.a. The patient underwent a surgery on heft left breast cancer. It recurred in her left chest wall seven years later, resulting in the formation of a carcinomatous ulcer. This carcinomatous ulcer became resistant to the cryosurgery and carcinostatic chemotherapy, leading to need for the radiotherapy. The patient was exposed to a total radiation dose of 40 Gy while using oily bleomycin and carmofur ointment in combination with a view toward enhancing the effects of the radiotherapy. Upon peroral administration of zinc sulfate and injection of intaserine to facilitate wound healing, the ulcer became cancer-free and an eschar was produced. However, she fell down accidently at this stage and the wound was traumatized and ulcerated again. Thus, cythocrome c was injected and at the same time, Bendazac ointment was applied. The epithelialization did not proceed any further although some erythema and hyperemia were still observed at the infected site. At this stage, the coating of a therapeutic preparation to be described in Example 1, which pertains to the present invention, was started. Effects of the treatment were observed within 24 hours as reduction to spontaneous pains and exudate. Four days later, the epithelialization of the surrounding area was observed together with the formation of benign granulation tissue over the surface of the ulcer. The wound was covered by a thick cuticule before the 20th day, resulting in disappearance of the ulcer. The thus-cured skin was thereafter resistant to usual extrinsic forces.

Case 2

Female, 73 y.o.a. This patient was subjected to postoperative radiation for the treatment of cervical cancer 18 years before. Her lower abdomen was infected by a radiation ulcer. Some scars were formed there. It was atrophic. Besides pigmentation, telangiectasia and ulcer formation were also observed. In the Case, the hyperbaric oxygen therapy, zinc sulfate, injectable glutathione, injectable intaserine and Bendazac ointment were applied intermittently in combination. However, the ulcer was not improved. The oral ubidecarenone therapy as also applied for further 2 months but no change was observed as to the ulcer. Thus, the coating of a therapeutic preparation to be described in Example 1, which pertains to this invention, was initiated. The ulcer healed up in two weeks and the pigmentation and telangietasia were improved.

The invention will hereinafter be described more specifically in the following Examples:

EXAMPLE 1

| | |
|---|---|
| Stearyl alcohol | 5 wt/% |
| Stearic acid | 2 |
| Hydrogenated lanolin | 2 |
| Squalane | 6 |
| Isopropyl myristate | 4 |
| Polyoxyethylene (25 moles) cetyl alcohol ether | 3 |
| Glycerin monostearate | 2 |
| Ubidecarenone | 0.3 |
| Propylene glycol | 5 |
| Butyl paraben | 0.2 |
| Antioxidant | as needed |
| Perfume | as needed |
| Purified water | 70.5 |

The above components were mixed in a manner known per se in the art into a homogeneous cream as a therapeutic preparation of this invention.

EXAMPLE 2

| | |
|---|---|
| Cetyl alcohol | 4 wt. % |
| Behenic acid | 2.5 |
| Vaseline | 3 |
| Liquid paraffin | 10 |
| 2-Octyldodecyl alcohol | 4 |
| Bees wax | 1 |
| Glycerin monsterate | 2 |
| Polyoxyethylene (20 moles) sorbitan monolaurate | 2 |
| Ubidecarenone | 1 |
| Glycerin | 5 |
| Polyethyelene glycol 1500 | 5 |
| Caustic potash | 0.2 |
| Ethylparaben | 0.4 |
| Perfume | as needed |
| Purified water | 59.9 |

The above components were mixed in a manner known per se in the art into a homogeneous cream as a therapeutic preparation of this invention.

EXAMPLE 3

| | |
|---|---|
| Stearic acid | 2 wt. % |
| Cetyl alcohol | 0.8 |
| Bees wax | 1 |
| Squalane | 3 |
| Olive oil | 1 |
| Polyoxyethylene (10 moles) monooleate | 2 |
| Glycerin | 5 |
| Ethanol | 3 |
| Carboxyvinyl polymer | 0.2 |
| Triethanol amine | 1.2 |
| Ubidecarenone | 0.1 |
| Antioxidant | as needed |
| Perfume | as needed |
| Butylparaben | 0.3 |
| Purified water | 80.4 |

The above components were mixed in a manner known per se in the art into a homogeneous lotion as a therapeutic preparation of this invention.

EXAMPLE 4

| | |
|---|---|
| Liquid paraffin | 5 wt. % |
| Vaseline | 2 |
| Cetanol | 1 |
| Glycerin monostearate | 2 |
| Polyoxyethylene (20 moles) sorbitan monolaurate | 1 |
| Ubidecarenone | 0.5 |
| Dipropylene glycol | 5 |
| Xanthan gum | 1 |
| Methylparaben | 0.2 |
| Antioxidant | as needed |
| Perfume | as needed |
| Purified water | 82.3 |

The above component were mixed in a manner known per se in the art into a homogeneous lotion as a therapeutic preparation of this invention.

Having now fully described the invention, it will be apparent to one of ordinary skill in the art that many changes and modifications can be made thereto without departing from the spirit or scope of the invention as set forth herein.

What is claimed is:

1. In a therapeutic method for treating radiation ulcers, the improvement wherein ubidecarenone is cutaneously applied in an effective amount for treating radiation ulcers.

2. A method as claimed in claim 1, wherein ubidecarenone is cutaneously applied in combination of cytochrome c and/or urokinase.

3. A method as in claim 1 in which ubidecarenone is used in a preparation for treating radiation ulcers in an amount of 0.05–5 wt. %.

* * * * *